(12) United States Patent
Yuki et al.

(10) Patent No.: US 9,259,416 B2
(45) Date of Patent: Feb. 16, 2016

(54) PYRAZOLONE COMPOUNDS USEFUL FOR TREATMENT OF CEREBROVASCULAR DISORDERS ASSOCIATED WITH ISCHEMIC STROKE

(75) Inventors: Satoshi Yuki, Tokyo (JP); Takuma Nakano, Tokyo (JP); Hiroko Suzuki, Tokyo (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 1332 days.

(21) Appl. No.: 11/659,799

(22) PCT Filed: Aug. 10, 2005

(86) PCT No.: PCT/JP2005/014969
§ 371 (c)(1),
(2), (4) Date: May 30, 2007

(87) PCT Pub. No.: WO2006/016707
PCT Pub. Date: Feb. 16, 2006

(65) Prior Publication Data
US 2007/0249700 A1 Oct. 25, 2007

(30) Foreign Application Priority Data
Aug. 10, 2004 (JP) .................................. 2004-233635

(51) Int. Cl.
*A61K 31/4152* (2006.01)
*A61K 39/00* (2006.01)

(52) U.S. Cl.
CPC ....... *A61K 31/4152* (2013.01); *A61K 2039/545* (2013.01)

(58) Field of Classification Search
CPC .................................................. A61K 31/4152
See application file for complete search history.

(56) References Cited

U.S. PATENT DOCUMENTS

2007/0043116 A1* 2/2007 Funakoshi et al. ............ 514/558

FOREIGN PATENT DOCUMENTS

| EP | 0 208 874 | 1/1987 |
|---|---|---|
| JP | 3-215425 | 9/1991 |
| JP | 3-215426 | 9/1991 |
| JP | 2004-91441 | 3/2004 |
| JP | 2004123700 A * | 4/2004 |

OTHER PUBLICATIONS

Hata et al (Pulse Radiolysis Study on Free Radical Scavenger Edaravone(3-methyl-1-phenyl-2-pyrazolin-5-one).2: A Comparative Study on Edaravone Derivatives, 2011, Journal of Radiation Research, vol. 52, pp. 15-23).*

Takahashi et al (MCI-186 prevents spinal cord damage and affects enzyme levels of nitric oxide synthase and Cu/Zn superoxide dismutase after transient ischemia in rabbits, Nov. 2003, The Journal of Thoracic and Cardiovascular Surgery, vol. 126, p. 1461-1466).*
Faden et al (Archives of Neurology, 2007, vol. 64, pp. 794-800).*
Kabadi et al (International Journal of Molecular Science, 2014, vol. 15, pp. 1216-1236).*
Alberts (Stroke, 2004, vol. 35, pp. 342-344).*
JP 2004/123700 (Derwent abstract, Apr. 22, 2004).*
JP 2004/123700 (English translation from Espacenet, printed on Feb. 17, 2015, Japanese document published in Apr. 2004).*
Noriko Yasuoka et al., "Neuroprotection of Edaravone on Hypdxic-Ischemic Brain Injury in Neonatal Rats", Brain Research, Development Brain Research, Jul. 19, 2004, vol. 151, No. 1-2, pp. 129-139.
H. Shibata, et al., "Phase I Clinical Study of MCI-186 (Edaravne, 3-Methyl-1-Phenyl-2-Pyrazolin-5-One) in Healthy Volunteers: Safety and Pharmacokinetics of Single and Multiple Administrations", Rinsho Yakuri—Japanese Journal of Clinical Pharmacology and Therapeutics, Nihon Rinsho Yakuri Gakkai, Tokyo, Japan, vol. 29, No. 6, Nov. 1998, pp. 863-876.
"Effect of a Novel Free Radical Scavenger, Edaravone (MCI-186), on Acute Brain Infarction, Randomized, Placebo-Controlled, Double=Blind Study At Multicenters", Cerebrovascular Diseases, Karger, Basel, CH, vol. 15, No. 3, 2003, pp. 222-229.
Li-Hui Zhang et al., Database Medline [Online] US National Library of Medicine (NLM), Bethesda, MD, US; Dec. 2003, "Neuroprotective effect of ONO-1078, a leukotriene receptor antagonist, on transient global cerebal ischemia in rats", XP002386754.
H. Nakamura et al., "Effects of Edaravone on Experimental Brain Injury in View of Free Radical Reaction", ACTA Neurochirurgica. Supplement. 2003, vol. 86, pp. 309-311.
Tomoaki Ikeda et al., "Effect of the Free Radical Scavenger, 3-Methyl-1-Phenyl-2-Pyrazolin-5-One (MCI-186), on Hypoxia-Ischemia-Induced Brain Injury in Neonatal Rats", Neuroscience Letters, Limerick, IE, vol. 329, No. 1, 2002, pp. 33-36.

(Continued)

*Primary Examiner* — Sean Basquill
*Assistant Examiner* — Mark V Stevens
(74) *Attorney, Agent, or Firm* — Wenderoth, Lind & Ponack LLP

(57) ABSTRACT

A drug for the treatment of cerebrovascular disorders associated with insufficient cerebral circulation such as ischemic stroke, which comprises a pharmaceutically effective amount of a pyrazolone compound of structural Formula (I):

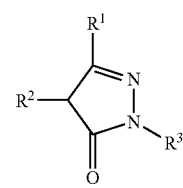

or a pharmaceutically acceptable salt thereof, or a pseudo-polymorphic form thereof, administered at a controlled dose so that the plasma concentration of unchanged form is kept constant for a predetermined period of time and so that the compound may exhibit a higher effect.

7 Claims, 4 Drawing Sheets

(56) References Cited

OTHER PUBLICATIONS

Kazunori Toyoda et al., "*Free Radical Scavenger, Edaravone, in Stroke With Internal Carotid Artery Occlusion*", Journal of the Neurological Sciences. Jun. 15, 2004, vol. 221, No. 1-2, pp. 11-17.

T. Watanabe et al., "*Effects of an Antistroke Agent MCI-186 on Cerebral Arachidonate Cascade*", The Journal of Pharmacology and Experimental Therapeutics, Dec. 2004, vol. 271, No. 3, pp. 1624-1629.

T. Yamamoto et al., "*Delayed Neuronal Death Prevented by Inhibition of Increased Hydroxyl Radical Formation in a Transient Cerebral Ischemia*", Brain Research, Jul. 11, 1997, vol. 762, No. 1-2, pp. 240-242.

Database WPI, Section Ch, Week 200382, Derwent Publications Ltd., London, GB; AN 2003-878221, XP002386756.

Minako Yamamoto et al., "*3-Methyl-1-Phenyl-2-Pyrazolin-5-One(MCI-186): Protein Binding and Distribution to Red Blood Cell*", Jpn Pharmacol Ther, vol. 25, Supplemental 97, pp. 245-253.

Chinese Official Action dated Oct. 9, 2009 with English translation.

Z. Yang et al., "Edaravone, an ethical brain protecting agent for acute cerebral infarction", Chinese Journal of New Drugs, vol. 11, No. 12, pp. 911-913, 2002.

T. Nakagomi et al., "Effect of Edaravone on Cerebral Vasospasm Following Experimental Subarachnoid Hemorrhage", Journal of Stroke and Cerebrovascular Diseases, vol. 12, No. 1, pp. 17-21, 2003.

K. Ohtani et al., "SM-31900, a novel NMDA receptor glycine-binding site antagonist, reduces infarct volume induced by permanent middle cerebral artery occlusion in spontaneously hypertensive rats", Neurochemistry International, vol. 42, No. 5, pp. 375-384, 2003.

J. Kucharczyk et al., "Nicardipine reduces ischemic brain injury. Magnetic resonance imaging/spectroscopy study in cats", Stroke, vol. 20, No. 2, pp. 268-274, 1989.

N. Morimoto, "Effects of heparin-urokinase on the brain damage induced by complete global brain ischemia", Journal of Okayama Medical Association, vol. 103, pp. 173-181, 1991.

J. Bailey, "An Approximate Model-Independent Method to Maintain Constant Plasma Levels of Intravenous Drugs", Journal of Pharmacokinetics and Biopharmaceutics, vol. 19, No. 6, pp. 635-645, 1991.

European Search Report issued Sep. 4, 2012 in corresponding European Patent Application No. 05 772 671.3.

Ohta et al., "Effects of Continuous Intravenous Infusion of MCI-186 on Functional Recovery after Spinal Cord Injury in Rats", Journal of Neurotrauma, vol. 28, Feb. 2011, pp. 289-298.

Office Action issued Jul. 9, 2013 in corresponding Canadian Application No. 2,576,544.

\* cited by examiner

Fig. 2-a
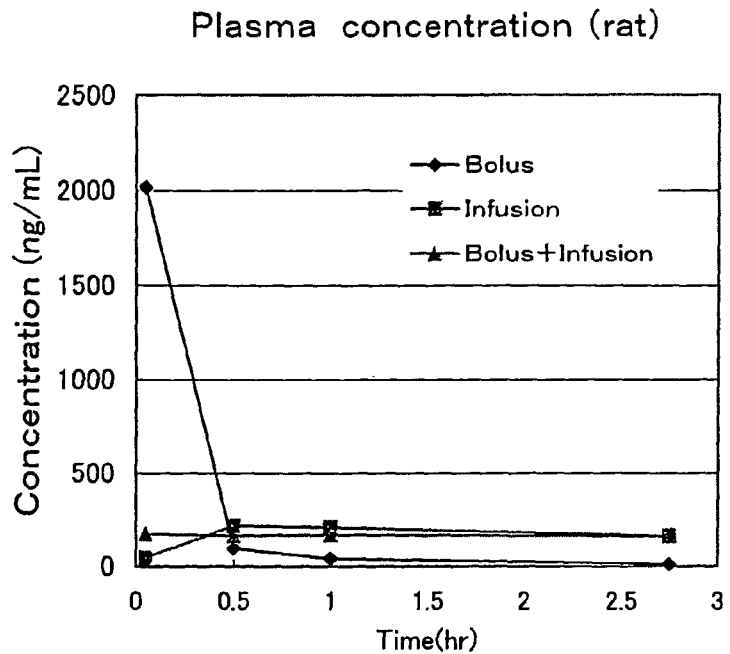
Fig. 2-b
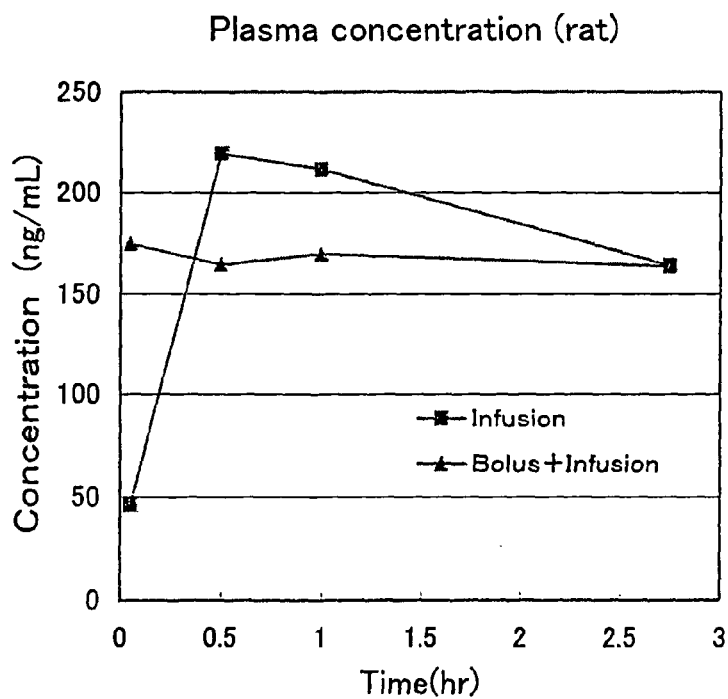

Fig. 3-a
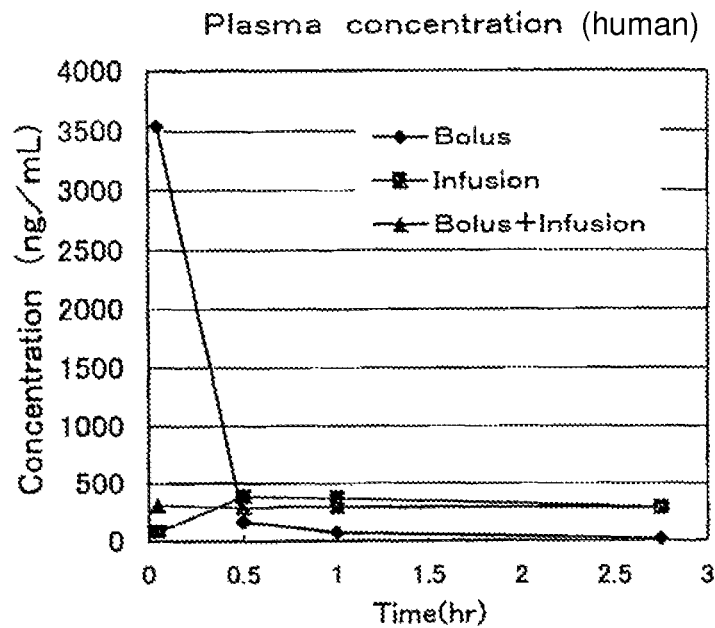
Fig. 3-b
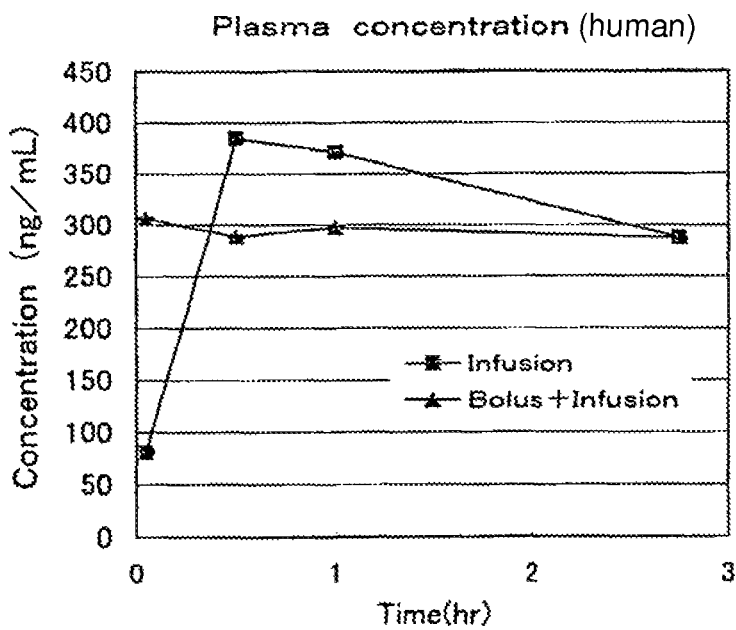

PYRAZOLONE COMPOUNDS USEFUL FOR TREATMENT OF CEREBROVASCULAR DISORDERS ASSOCIATED WITH ISCHEMIC STROKE

This application is a U.S. National Stage of International Application No. PCT/JP2005/014969, filed Aug. 10, 2005.

TECHNICAL FIELD

The present invention relates to treatment of cerebrovascular disorders associated with insufficient cerebral circulation. The invention comprises administration to a patient in need of such treatment of a loading dose followed by a maintenance dose of a therapeutically effective amount of a pyrazolone compound of Formula (I):

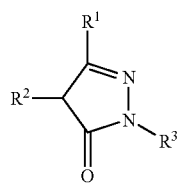

or a pharmaceutically acceptable salt of the compound, or a psudeo-polymorphic form (hydrate or solvate) or mixture of such forms:
wherein,
$R^1$ represents a hydrogen atom, an aryl group, an alkyl group having from 1 to 5 carbon atoms or an alkoxycarbonylalkyl group having from 3 to 6 carbon atoms in total;
$R^2$ represents a hydrogen atom, an aryloxy group, an arylmercapto group, an alkyl group having from 1 to 5 carbon atoms or a hydroxyalkyl group having from 1 to 3 carbon atoms, or $R^1$ and $R^2$ taken together may form an alkylene group having from 3 to 5 carbon atoms; and
$R^3$ represents a hydrogen atom, an alkyl group having from 1 to 5 carbon atoms, a cycloalkyl group having from 5 to 7 carbon atoms, a hydroxyalkyl group having from 1 to 3 carbon atoms, a benzyl group, a naphthyl group or a phenyl group, or a phenyl group substituted with from 1 to 3 substituents, which substituent(s) may be the same or different and are selected from the class consisting of alkoxy groups having from 1 to 5 carbon atoms, hydroxyalkyl groups having from 1 to 3 carbon atoms, alkoxycarbonyl groups having from 2 to 5 carbon atoms in total, alkylmercapto groups having from 1 to 3 carbon atoms, alkylamino groups having from 1 to 4 carbon atoms, dialkylamino groups having from 2 to 8 carbon atoms in total, halogen atoms, a trifluoromethyl group, a carboxyl group, a cyano group, a hydroxyl group, a nitro group, an amino group, and an acetamide group.

Cerebrovascular disorders can be caused by insufficient cerebral circulation as a result of, for illustrative purposes only and not limiting the scope of the invention or its application, ischemic stroke and transient ischemic attacks, in which a blood vessel supplying cerebral blood supply becomes occluded. Insufficient blood flow decreases the flow of blood, which deprives affected brain tissue of oxygen, causing brain ischemia and consequent neurologic symptoms.

Further referring to ischemic stroke as illustrative, the treatment of ischemic stroke is generally selected from two approaches: 1) treatment in the acute stage for the purpose of removing the ischemia and inhibiting ischemia-caused cytopathy; and 2) treatment in the chronic stage for treating the sequelae of ischemic stroke.

The present invention is intended for purposes of both approaches—treatment in the acute stage and the chronic stage of ischemic stroke.

Disorders implicated in obstruction of blood vessels, insufficient cerebral circulation, and ischemic syndromes include.

Ischemic stroke and other ischemic syndromes may cause cytopathy. Examples of disorders caused by cytopathy are disorders associated with neurological symptoms, such as neuropsychologic symptoms and somatoneurological symptoms. Specific examples of disorders associated with neuropsychologic symptoms include:

1. consciousness symptoms (associated disorders such as consciousness disorder; akinesic mutism);
2. attention symptoms (associated disorders such as acute confusional state; half-side space neglect);
3. memory symptoms (associated disorders such as episode memory; amnestic syndrome);
4. speech symptoms (associated disorders such as aphasia, agraphia, alexia); function symptoms (associated disorders such as apraxia);
5. cognition symptoms (associated disorders such as agnosia);
6. intelligence symptoms (associated disorders such as dementia); and
7. associated disorders of other symptoms of, for example, affection, character change, hallucination, delusion.

Specific examples of somatoneurological symptoms with associated disorders include:

1. cranial nerve symptoms (e.g., opthalmopathy symptoms, facial spasm and associated disorders such as sensory disorder); and optic nerve symptoms (such as homonymous hemianopia); opthalmopathy symptoms (left and right difference in fissures of eye (blepharoptosis)); ocular position (conjugate deviation of eyes, skew deviation of eyes); ocular motion (horizontal, vertical); abnormal ocular motion (ocular bobbing); nystagmus, pupilla (size, shape); light reflex;
2. Kinetic system symptoms (such as the presence or absence of spasm, indicated by Barre sign, Mingazzini test, drop test, Hoover sign, muscular tonus, facial spasm);
3. Sensory system symptoms (such as those associated with sensory disorder: right and left difference, dissociation sensibility (hot algesthesia vs taction, deep sensibility);
4. Coordinated motion symptoms (such as uncoordination symptoms (such as limb motion ataxia, trunk motion ataxia), motion conversion, nose-pointing test, knee-heel test, leg-knocking test);
5. Reflex symptoms (such as deep reflex, morbid reflex (Babinski sign and Chaddock sign);
6. Autonomic nerve symptoms (such as ischuria, incontinence of urine, constipation, dyshidrosis);
7. Stand-up, walk symptoms (not positively carried out in the extra-acute stage of cerebral blood vessel disorder) (such as stand-up (on both legs, on one leg), hopping, walking, tandem gate-walking, Romberg sign, squat-down test);
8. meninx stimulus sign symptoms (such as poll tetany, Kerning sign);
9. Rigidity symptoms (such as decerebrate rigidity, decorticate rigidity).

Accordingly, the compounds of formula I of the invention are effective for the improvement of neurological symptoms associated with, for example, ischemic stroke as illustrative of a cause of insufficient cerebral circulation resulting in cerebrovascular disorders. In addition, the active ingredient is effective for the improvement of prognosis associated with ischemic stroke and other causes of insufficient cerebral circulation, and improvement of interference with activities of daily living and/or relief of disability. In particular, the compounds of formula I of the invention are effective for improvement of neurological symptoms, interference with activities of daily living and disability at the acute stage of ischemic stroke, and other consequences of ischemic syndrome.

The NIH stroke scale (NIHSS) is known for the purpose of objective and quantitative determination of neurological criticality. Patients to whom the compounds of the invention may be administered are not limited with respect to determination by the NIH stroke scale, but for purposes of illustration preferably include patients having an NIH stroke scale of not more than 22.

Other than the NIHSS, objective and quantitative known methods of determination for neurological criticality include the Canadian neurological scale (CNS), Glasgow Coma scale (GCS), hempispheric stroke scale, Hunt & Hess scale, Mathew stroke scale, mini-mental state examination (MMSE), Orgogozo stroke scale, Oxfordshire Community stroke project classification (Bamford), Scandinavian stroke scale, Japan Coma scale (JCS), and Japan stroke scale (JSS). Using these determination methods, but without limitation, the patients may have a scale that corresponds to the NIH stroke scale of not more than 22.

The route of administration to a patient of a pharmaceutical composition of the invention comprising a pharmaceutically effective amount of a pyrazolone compound of structural Formula (I) is not limited. The pharmaceutical composition is preferably administered parenterally, but alternatively may be administered orally. The pharmaceutical composition may be administered intravenously or percutaneously, but preferably intravenously.

It has been verified that the safety of the above-mentioned compounds of formula I for the active ingredient of the pharmaceutical composition of the invention is high (mouse intraabdominal administration $LD_{50}$=2012 mg/kg; rat oral administration $LD_{50}$=3,500 mg/kg; Registry of Toxic Effects of Chemical Substances, 1981-1982), and that the compounds are not carcinogenic (National Cancer Institute Report, 89, 1978).

The pyrazolone compounds represented by formula (I) are known to have a cerebral function normalizing effect (JP-B 5-31523), a lipid peroxide formation inhibiting effect (JP-B 5-35128, compound of Example 1), an antiulcer effect (JP-A 3-215425), and a hyperglycemia inhibiting effect (JP-A 3-215426). Such compounds have been produced and marketed since 2001 as a brain-protecting drug under the general name Edaravone and trade name Radicut® by Mitsubishi Pharma Corporation.

The potency and the effectiveness of Edaravone approved by the Ministry of Labor, Health and Welfare of Japan are for the improvement of neurological symptoms, interference with activities of daily living and disability each associated with acute ischemic stroke and the use and the dose of the drug are as follows: In general, for administration to an adult, one tube (30 mg as Edaravone) is diluted with a suitable amount of physiological saline or the like, and the dilution is administered to an adult patient by intravenous drip twice a day in the morning and in the evening, each taking 30 minutes. Therefore, according to the approved use and dope thereof, it is a well-known fact that Edaravone is effective for ischemic stroke.

The inventors are aware of a published report about the plasma concentration profile of an unchanged form of Edaravone following administration by intravenous infusion of Radicut® to healthy male volunteers. (Hisao Shibata et al., Clinical Pharmacology, 29: 863-876, 1998). In addition, there are many reports relating to the pharmacological evaluation of Edaravone in animals other than humans. However, to the inventors' knowledge, all of the above mentioned reports, as well as others, disclose a single form of administration among, for example, intravenous bolus administration, intravenous infusion, oral administration (e.g., JP-A 2004-91441), subcutaneous bolus administration, or intra-abdominal bolus administration. To the best of the inventors' knowledge, there is no report that discloses combined use of these forms of administration, and specifically, no report disclosing a combined use of a loading dose administration and a maintenance dose administration after—for example, combining intravenous bolus administration followed by intravenous infusion. Again to the best of the inventors' knowledge, there is no report of the plasma concentration profile of an unchanged form of a pyrazolone compound of formula I following such combined administration. See, for example, Japanese patents JP-B 5-31523, JP-B 5-35128, JP-A 3-215425, and JP-A 3-215426, non-patent reference Hisao Shibata et al., Clinical Pharmacology, 29: 863-876, 1998, and reference JP-A 2004-91441.

The inventors have found that the compound according to the invention provides, as an active ingredient, a pyrazolone compound that satisfies a need in the pharmaceutical market for improved potency useful for the treatment of disorders associated with ischemic stroke.

The present inventors have found that, when the dose of a pyrazolone compound of formula I is controlled so as to substantially constantly maintain the plasma concentration of unchanged form or the free plasma consentration of the compound at a predetermined level for a predetermined period of time, then the potency of the compound for treatment of disorders associated with ischemic stroke can be improved.

Specifically, the invention relates to a method for the treatment of cerebrovascular disorders associated with insufficient cerebral circulation mentioned below:

1. A method for the treatment of cerebrovascular disorders associated with insufficient cerebral circulation, comprising administration to a patient in need of such treatment of a therapeutically effective amount of a compound of Formula (I),

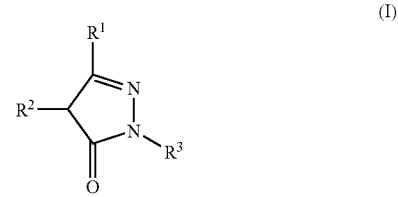

wherein,
$R^1$ represents a hydrogen atom, an aryl group, an alkyl group having from 1 to 5 carbon atoms or an alkoxycarbonylalkyl group having from 3 to 6 carbon atoms in total;
$R^2$ represents a hydrogen atom, an aryloxy group, an arylmercapto group, an alkyl group having from 1 to 5 carbon atoms or a hydroxyalkyl group having from 1 to 3 carbon atoms, or $R^1$ and $R^2$ taken together may form an alkylene group having from 3 to 5 carbon atoms; and
$R^3$ represents a hydrogen atom, an alkyl group having from 1 to 5 carbon atoms, a cycloalkyl group having from 5 to 7 carbon atoms, a hydroxyalkyl group having from 1 to 3 carbon atoms, a benzyl group, a naphthyl group or a phenyl group, or a phenyl group substituted with from 1 to 3 substituents, which substituent(s) may be the same or different and are selected from the class consisting of alkoxy groups having from 1 to 5 carbon atoms, hydroxyalkyl groups having from 1 to 3 carbon atoms, alkoxycarbonyl groups having from 2 to 5 carbon atoms in total, alkylmercapto groups having from 1 to 3 carbon atoms, alkylamino groups having from 1 to 4 carbon atoms, dialkylamino groups having from 2 to 8 carbon atoms in total, halogen atoms, a trifluoromethyl group, a carboxyl group, a cyano group, a hydroxyl group, a nitro group, an amino group, and an acetamide group, or a pharmaceutically acceptable salt of the compound, or a pseudo-polymorphic form, or a mixture of such forms, and further wherein the dosage of administration is controlled for providing rapid attainment of a therapeutically effective plasma concentration of unchanged form of the compound, and for providing substantially continuous maintenance of a therapeutically effective plasma concentration of unchanged form of the compound.

2. A method according to item 1, wherein the dosage is controlled for providing the plasma concentration of unchanged form of the compound within a range of from about 60 ng/ml to about 3200 ng/ml within about 3 minutes to about 5 minutes after completion of the dosage administration, and for providing maintenance of the plasma concentration within a range of from about 60 ng/ml to about 3200 ng/ml up to a period of about 120 hours after initiation of the maintenance administration.

3. A method according to item 1, wherein the compound is administered by a loading dose for providing the plasma concentration of unchanged form of the compound within a range of from about 60 ng/ml to about 3200 ng/ml within about 3 minutes to about 5 minutes after completion of the loading dose administration, and further wherein the compound is administered by a maintenance dose for providing the plasma concentration of unchanged form of the compound within the range of from about 60 ng/ml to about 3200 ng/ml up to about 120 hours after initiation of the maintenance dose administration.

4. A method according to item 1, wherein the dosage is controlled for providing the free plasma concentration of unchanged form of the compound within a range of from about 5 ng/ml to about 260 ng/ml within about 3 minutes to about 5 minutes after completion of the initial dosage administration, and for providing the free plasma concentration of unchanged form of the compound within a range of from about 5 ng/ml to about 260 ng/ml for about 0.5 hours to about 120 hours after initiation of the administration of the maintenance dose.

5. A method according to item 1, in which the compound is administered by a loading dose for providing a free plasma concentration of unchanged form of the compound within a range of from about 5 ng/ml to about 260 ng/ml within about 3 minutes to about 5 minutes after completion of the administration of the loading dose, and is administered by a maintenance dose for providing a free plasma concentration of unchanged form of the compound within a range of from about 5 ng/ml to about 260 ng/ml for about 0.5 hours to about 120 hours after initiation of the administration of the maintenance dose.

6. A method according to item 1, wherein rapid attainment of a therapeutically effective plasma concentration of unchanged form of the compound is achieved by intravenous bolus administration, and further wherein substantially continuous maintenance of a therapeutically effective plasma concentration at a desired level for a desired period of time is achieved by intravenous infusion.

7. A method according to item 1, wherein insufficient cerebral circulation is related to ischemia, including ischemic stroke and transient ischemic attack.

8. A method for the treatment of cerebrovascular disorders associated with insufficient cerebral circulation related to ischemia, comprising administration to a patient in need of such treatment of a loading dose and a maintenance dose of a therapeutically effective amount of the compound of Formula (I),

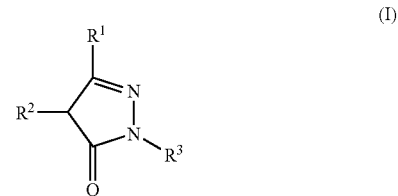

wherein, $R^1$ represents a hydrogen atom, an aryl group, an alkyl group having from 1 to 5 carbon atoms or an alkoxycarbonylalkyl group having from 3 to 6 carbon atoms in total, $R^2$ represents a hydrogen atom, an aryloxy group, an arylmercapto group, an alkyl group having from 1 to 5 carbon atoms or a hydroxyalkyl group having from 1 to 3 carbon atoms, or $R^1$ and $R^2$ taken together form an alkylene group having from 3 to 5 carbon atoms, $R^3$ represents a hydrogen atom, an alkyl group having from 1 to 5 carbon atoms, a cycloalkyl group having from 5 to 7 carbon atoms, a hydroxyalkyl group having from 1 to 3 carbon atoms, a benzyl group, a naphthyl group or a phenyl group, or a phenyl group substituted with from 1 to 3 substituents, which substituent(s) may be the same or different and are selected from the class consisting of alkoxy groups having from 1 to 5 carbon atoms, hydroxyalkyl groups having from 1 to 3 carbon atoms, alkoxycarbonyl groups having from 2 to 5 carbon atoms in total, alkylmercapto groups having from 1 to 3 carbon atoms, alkylamino groups having from 1 to 4 carbon atoms, dialkylamino groups having from 2 to 8 carbon atoms in total, halogen atoms, a trifluoromethyl group, a carboxyl group, a cyano group, a hydroxyl group, a nitro group, an amino group and an acetamide group, or a pharmaceutically acceptable salt, of the compound, or a pseudo-polymorphic form, or a mixture of such forms, and further wherein (i) the compound is administered by intravenous bolus administration of a loading dose for providing rapid attainment, within about 3 minutes to about 5 minutes after completion of the administration of the loading dose, of the plasma concentration of unchanged form of the compound within a range of from about 60 ng/ml to about 3200 ng/ml, or of the free plasma concentration of unchanged form of the compound within a range of from about 5 ng/ml to about 260 ng/ml, and (ii) the compound is administered by intravenous infusion administration of a maintenance dose, for from about 0.5 hours to about 120 hours after initiation of the administration of the maintenance dose, for maintaining the plasma concentration of unchanged form of the compound substantially within a range of from about 60 ng/ml to about 3200 ng/ml or for maintaining the free plasma concentration of unchanged form of the compound substantially within a range of from about 5 ng/ml to about 260 ng/ml.

9. The method according to item 8, wherein the range of plasma concentration of unchanged form of the compound within about 3 minutes to about 5 minutes after completion of the loading dose administration, and the range of the desired maintenance plasma concentration of unchanged form of the compound is selected from the group comprising from about 180 ng/ml to about 430 ng/ml; from about 180 ng/ml to about 800 ng/ml; from about 180 ng/ml to about 930 ng/ml; from about 180 ng/ml to about 1240 ng/ml; and from about 180 ng/ml to about 1600 ng/ml.

10. The method according to item 8, wherein the range of free plasma concentration of unchanged form of the compound attained within about 3 minutes to about 5 minutes after completion of the loading dose administration, and the range of the desired maintenance free plasma concentration of unchanged form of the compound is selected from the group comprising from about 15 ng/ml to about 35 ng/ml; from about 15 ng/ml to about 50 ng/ml; from about 15 ng/ml to about 65 ng/ml; from about 15 ng/ml to about 75 ng/ml; from about 15 ng/ml to about 100 ng/ml; and from about 15 ng/ml to about 130 ng/ml.

11. The method according to item 8, wherein the range of free plasma concentration of unchanged form of the compound within about 3 minutes to about 5 minutes after completion of the loading dose administration, and the range of the desired maintenance free plasma concentration of unchanged form of the compound is selected from the group comprising from about 15 ng/ml to about 35 ng/ml; from about 15 ng/ml to about 50 ng/ml; from about 15 ng/ml to about 65 ng/ml; from about 15 ng/ml to about 75 ng/ml; from about 15 ng/ml to about 100 ng/ml; and from about 15 ng/ml to about 130 ng/ml.

12. The method according to item 8, wherein the desired duration of about 120 hours after initiation of the administration of the maintenance dose is selected from the group consisting of within about 120 hours; within about 72 hours; within about 24 hours, or within about 12 hours; within about 3 hours; within about 1 hour; and within 0.5 hours.

13. A method for the treatment of cerebrovascular disorders associated with insufficient cerebral circulation, comprising administration to a patient in need of such treatment of a therapeutically effective amount of a compound of Formula (I),

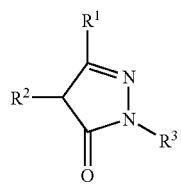

wherein, $R^1$: represents a hydrogen atom, an aryl group, an alkyl group having from 1 to 5 carbon atoms or an alkoxycarbonylalkyl group having from 3 to 6 carbon atoms in total;

$R^2$ represents a hydrogen atom, an aryloxy group, an arylmercapto group, an alkyl group having from 1 to 5 carbon atoms or a hydroxyalkyl group having from 1 to 3 carbon atoms, or $R^1$ and $R^2$ taken together may form an alkylene group having from 3 to 5 carbon atoms; and $R^3$ represents a hydrogen atom, an alkyl group having from 1 to 5 carbon atoms, a cycloalkyl group having from 5 to 7 carbon atoms, a hydroxyalkyl group having from 1 to 3 carbon atoms, a benzyl group, a naphthyl group or a phenyl group, or a phenyl group substituted with from 1 to 3 substituents, which substituent(s) may be the same or different and are selected from the class consisting of alkoxy groups having from 1 to 5 carbon atoms, hydroxyalkyl groups having from 1 to 3 carbon atoms, alkoxycarbonyl groups having from 2 to 5 carbon atoms in total, alkylmercapto groups having from 1 to 3 carbon atoms, alkylamino groups having from 1 to 4 carbon atoms, dialkylamino groups having from 2 to 8 carbon atoms in total, halogen atoms, a trifluoromethyl group, a carboxyl group, a cyano group, a hydroxyl group, a nitro group, an amino group, and an acetamide group, or a pharmaceutically acceptable salt of the compound and further wherein the dosage of administration is controlled for providing rapid attainment of a therapeutically effective plasma concentration of unchanged form of the compound, and for providing substantially continuous maintenance of a therapeutically effective plasma concentration of unchanged form of the compound, and further wherein the dose for rapid attainment of a therapeutically effective plasma concentration of unchanged form of the compound is selected from a group consisting of from about 0.025 to about 1.3 mg per kg of the weight of a patient; about 0.075 to about 0.5 mg per kg of the weight of a patient; about 0.1 to about 0.3 mg per kg of the weight of a patient; about 0.15 to about 1.0 mg per kg of the weight of a patient; and about 0.25 to about 0.75 mg per kg of the weight of a patient, and the dose for maintenance of a therapeutically effective plasma concentration is administered from about 0.05 to about 2.5 mg/hr per kg of the weight of the patient for a period selected from the group consisting of about 0.5 hours; 1 hour; 2.75 hours; and 72 hours.

14. A method for the treatment of cerebrovascular disorders associated with insufficient cerebral circulation, comprising administration to a patient in need of such treatment of a therapeutically effective amount of a compound of Formula (I),

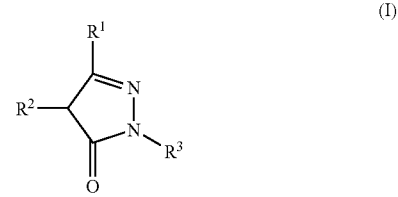

wherein, $R^1$ represents a hydrogen atom, an aryl group, an alkyl group having from 1 to 5 carbon atoms or an alkoxycarbonylalkyl group having from 3 to 6 carbon atoms in total;

$R^2$ represents a hydrogen atom, an aryloxy group, an arylmercapto group, an alkyl group having from 1 to 5 carbon atoms or a hydroxyalkyl group having from 1 to 3 carbon atoms, or $R^1$ and $R^2$ taken together may form an alkylene group having from 3 to 5 carbon atoms; and $R^3$ represents a hydrogen atom, an alkyl group having from 1 to 5 carbon atoms, a cycloalkyl group having from 5 to 7 carbon atoms, a hydroxyalkyl group having from 1 to 3 carbon atoms, a benzyl group, a naphthyl group or a phenyl group, or a phenyl group substituted with from 1 to 3 substituents, which substituent(s) may be the same or different and are selected from the class consisting of alkoxy groups having from 1 to 5 carbon atoms, hydroxyalkyl groups having from 1 to 3 carbon atoms, alkoxycarbonyl groups having from 2 to 5 carbon atoms in total, alkylmercapto groups having from 1 to 3 carbon atoms, alkylamino groups having from 1 to 4 carbon atoms, dialkylamino groups having from 2 to 8 carbon atoms in total, halogen atoms, a trifluoromethyl group, a carboxyl group, a cyano group, a hydroxyl group, a nitro group, an amino group, and an acetamide group, or a pharmaceutically acceptable salt of the compound, further wherein (i) the compound is administered by intravenous bolus administration of a loading dose for providing rapid attainment, within about 3 minutes to about 5 minutes after completion of the administration of the loading dose, of the plasma concentration of unchanged form of the compound within a range of from about 60 ng/ml to about 3200 ng/ml, or of the free plasma concentration of unchanged form of the compound within a range of from about 5 ng/ml to about 260 ng/ml, and (ii) the compound is administered by intravenous infusion administration of a maintenance dose, for from about 0.5 hours to about 120 hours after initiation of the administration of the maintenance dose, for maintaining the plasma concentration of unchanged form of the compound substantially within a range of from about 60 ng/ml to about 3200 ng/ml or for maintaining the free plasma concentration of unchanged form of the compound substantially within a range of from about 5 ng/ml to about 260 ng/ml.

and further wherein, the dose for rapid attainment of a therapeutically effective plasma concentration of unchanged form of the compound is selected from a group consisting of from about 0.025 to about 1.3 mg per kg of the weight of a patient; about 0.075 to about 0.5 mg per kg of the weight of a patient; about 0.1 to about 0.3 mg per kg of the weight of a patient; about 0.15 to about 1.0 mg per kg of the weight of a patient; and about 0.25 to about 0.75 mg per kg of the weight of a patient, and the dose for maintenance of a therapeutically effective plasma concentration is administered from about 0.05 to about 2.5 mg/hr per kg of the weight of the patient for a period selected from the group consisting of about 0.5 hours; 1 hour; 2.75 hours; and 72 hours.

15. A method according to item 1, 8, 13 or 14 wherein the compound of Formula (I) is 3-methyl-1-phenyl-2-pyrazolin-5-one.

16. A method according to item 1, 8, 13 or 14, wherein the treatment of cerebrovascular disorders is associated with acute ischemic stroke.

17. A method for the treatment of cerebrovascular disorders associated with insufficient cerebral circulation associated with acute ischemic stroke, comprising administration to a patient in need of such treatment of a loading dose and a maintenance dose of a therapeutically effective amount of the compound of Formula (I),

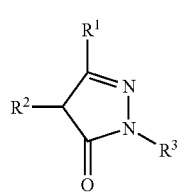

(I)

$R^1$ represents a hydrogen atom, an aryl group, an alkyl group having from 1 to 5 carbon atoms or an alkoxycarbonylalkyl group having from 3 to 6 carbon atoms in total, $R^2$ represents a hydrogen atom, an aryloxy group, an arylmercapto group, an alkyl group having from 1 to 5 carbon atoms or a hydroxyalkyl group having from 1 to 3 carbon atoms, or $R^1$ and $R^2$ taken together may form an alkylene group having from 3 to 5 carbon atoms, $R^3$ represents a hydrogen atom, an alkyl group having from 1 to 5 carbon atoms, a cycloalkyl group having from 5 to 7 carbon atoms, a hydroxyalkyl group having from 1 to 3 carbon atoms, a benzyl group, a naphthyl group or a phenyl group, or a phenyl group substituted with from 1 to 3 substituents, which substituent(s) may be the same or different and are selected from the class consisting of alkoxy groups having from 1 to 5 carbon atoms, hydroxyalkyl groups having from 1 to 3 carbon atoms, alkoxycarbonyl groups having from 2 to 5 carbon atoms in total, alkylmercapto groups having from 1 to 3 carbon atoms, alkylamino groups having from 1 to 4 carbon atoms, dialkylamino groups having from 2 to 8 carbon atoms in total, halogen atoms, a trifluoromethyl group, a carboxyl group, a cyano group, a hydroxyl group, a nitro group, an amino group and an acetamide group, or a pharmaceutically acceptable salt of the compound, or a pseudo-polymorphic form, or a mixture of such forms, wherein the compound of Formula (I) is 3-methyl-1-phenyl-2-pyrazolin-5-one.

and further wherein (i) the compound is administered by intravenous bolus administration of a loading dose for providing attainment of the plasma concentration of unchanged form of the compound within a range of from about 60 ng/ml to about 3200 ng/ml within about 3 minutes to about 5 minutes after completion of the administration of the loading dose, and for providing intravenous infusion administration of a maintenance dose for providing the plasma concentration of unchanged form of the compound within a range of from about 60 ng/ml to about 3200 ng/ml up to about 120 hours after initiation of administration of the maintenance dose; or (ii) the compound is administered by an intravenous bolus loading dose for providing the free plasma concentration of unchanged form of the compound within a range of from about 5 ng/ml to about 260 ng/ml within about 3 minutes to about 5 minutes after completion of the initial dose administration, and administration of a maintenance dose by intravenous infusion for providing the free plasma concentration of unchanged form of the compound within a range of from about 5 ng/ml to about 260 ng/ml for from about 0.5 hours to about 120 hours after initiation of the administration of the maintenance dose.

18. The method according to item 17, wherein the range of plasma concentration of unchanged form of the compound within about 3 minutes to about 5 minutes after completion of the loading dose administration, and the range of the desired maintenance plasma concentration of unchanged form of the compound is selected from the group comprising from about 180 ng/ml to about 430 ng/ml; from about 180 ng/ml to about 800 ng/ml; from about 180 ng/ml to about 930 ng/ml; from about 180 ng/ml to about 1240 ng/ml; and from about 180 ng/ml to about 1600 ng/ml.

19. The method according to item 17, wherein the range of free plasma concentration of unchanged form of the compound attained within about 3 minutes to about 5 minutes after completion of the loading dose administration, and the range of the desired maintenance free plasma concentration of unchanged form of the compound is selected from the group comprising from about 15 ng/ml to about 35 ng/ml; from about 15 ng/ml to about 50 ng/ml; from about 15 ng/ml to about 65 ng/ml; from about 15 ng/ml to about 75 ng/ml; from about 15 ng/ml to about 100 ng/ml; and from about 15 ng/ml to about 130 ng/ml.

20. The method according to item 17, wherein the range of free plasma concentration of unchanged form of the compound within about 3 minutes to about 5 minutes after completion of the loading dose administration, and the range of the desired maintenance free plasma concentration of unchanged form of the compound is selected from the group comprising from about 15 ng/ml to about 35 ng/ml; from about 15 ng/ml to about 50 ng/ml; from about 15 ng/ml to about 65 ng/ml; from about 15 ng/ml to about 75 ng/ml; from about 15 ng/ml to about 100 ng/ml; and from about 15 ng/ml to about 130 ng/ml.

21. The method according to item 17, wherein the desired duration of about 120 hours at the longest after initiation of the administration of the maintenance dose is selected from the group consisting of within about 120 hours; within about 72 hours; within about 24 hours, or within about 12 hours; within about 3 hours; within about 1 hour; and within 0.5 hours.

22. A method according to item 1, 8, 13, 14 or 17, wherein the treatment of cerebrovascular disorders is improvement of neurological symptoms, or of prognosis, or of interference with activities of daily living and/or disability, or a combination of such improvements.

23. A method according to item 1, 8, 13, 14 or 17, wherein patients in need of such treatment are determined by NIH stroke scale of not more than 22, or by a method of determination for neurological criticality corresponding to the NIH stroke scale of not more than 22.

24. A pharmaceutical composition comprised of a compound as recited in item 1, 8, 13, 14 or 17, and a pharmaceutically acceptable carrier thereof.

25. A pharmaceutical composition made by combining a compound as recited in item 1, 8, 13, 14 or 17, and a pharmaceutically acceptable carrier.

26. A process for preparing a pharmaceutical composition comprising combining a compound of item 1, 8, 13, 14 or 17, and a pharmaceutically acceptable carrier.

In general, when a drug is administered to a patient, it is metabolized into various metabolites. The term "unchanged form" as used by the inventors means the compound substantially is not metabolized (i.e., it remains the same compound as the administered compound). By the term "free plasma concentration of unchanged form," the inventors mean the plasma concentration of unchanged form not bound with protein. As illustrated, a compound of the present invention administered to a patient according to the present invention may be present in the plasma in unchanged form

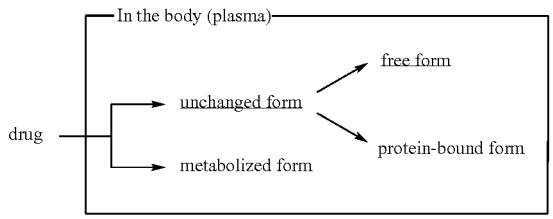

or a metabolized form. As unchanged form, the compound may be present as free form or as protein-bound form. In general, plasma concentration of unchanged form is the sum of free plasma concentration and protein-bound concentration of the particular drug. It is the free (unbound) form that is pharmacologically active. Since protein binding rates differ between species, the inventors have expressed the dose-action relationship of the compounds of this invention based on the free plasma concentration. Other published data use total plasma concentrations.

In accordance with the invention, the active ingredient comprised of a compound of formula I of the invention is administered at a loading dose followed by a maintenance dose. By the term "loading dose," the inventors mean the initial administration for rapidly reaching the effective concentration in plasma. By the term "maintenance dose," the inventors mean the substantially continuous administration sufficient for substantially maintaining the effective concentration of a therapeutically effective amount of the compound in plasma for a desired period of time. One example of the loading dose administration is bolus administration, and is preferably intravenous bolus administration. By the term "bolus administration," the inventors mean a route of administration capable of rapidly attaining the desired concentration in plasma.

Preferably, the administration of the loading dose is finished within about five minutes, more preferably within about 3 minutes. Examples, without limiting the invention, of the administration of a maintenance dose are drip infusion, oral administration, subcutaneous administration, and endermic administration. A preferred embodiment of administration of the maintenance dose is intravenous infusion.

Preferred embodiments of the drug for the treatment of disorders associated with ischemic stroke and other causes of insufficient cerebral circulation in the invention are mentioned below. It is desirable that a compound of the invention used as an active ingredient is administered so that the plasma concentration of the unchanged form of the compound is provided within the range of about 60 ng/ml to about 3200 ng/ml within about 3 minutes after completion of the loading dose administration, and thereafter is maintained within such range for a desired period. In the most preferred embodiment, the range of plasma concentration of unchanged form within about 3 minutes after completion of the loading dose administration, and thereafter at which the plasma concentration is maintained substantially in a range within about 180 ng/ml to about 430 ng/ml. In other embodiments of the invention, the range desired within about 3 minutes after completion of the loading dose administration may be from about 180 ng/ml to about 800 ng/ml, or from about 180 ng/ml to about 930 ng/ml, or from about 180 ng/ml to about 1240 ng/ml, or from about 180 ng/ml to about 1600 ng/ml.

When the plasma concentration of unchanged form is represented by the free plasma concentration of unchanged form, then it is desirable that the active ingredient is administered so that the free plasma concentration of unchanged form is provided within a range of from about 5 ng/ml to about 260 ng/ml within about 3 minutes after completion of the loading dose administration. In the most preferred embodiment from about 15 ng/ml to about 35 ng/ml. In other embodiments, the range may be from about 15 ng/ml to about 50 ng/ml, or from about 15 ng/ml to about 65 ng/ml, or from about 15 ng/ml to about 75 ng/ml, or from about 15 ng/ml to about 100 ng/ml, or from about 15 ng/ml to about 130 ng/ml.

In another embodiment of the invention, upon administration of the maintenance dose within about 3 minutes after completion of the loading dose administration, the plasma concentration of unchanged form or the free plasma concentration of unchanged form of the compound remains substantially within such ranges described above for the preferred embodiment and other embodiments upon administration of the loading dose.

Within about 3 minutes after completion of the loading dose administration, in the preferred embodiment of the invention it is desirable that the above-mentioned plasma concentration of unchanged form or free plasma concentration of unchanged form of the compound remains substantially as such within a period of about 120 hours after initiation of the loading dose administration. In other embodiments, the desired duration is within about 72 hours, or within about 24 hours, or within about 12 hours, or within about 3 hours, preferably within about 1 hour, or within 0.5 hours.

The inventors have defined the free plasma concentration of unchanged form to fall within the range of from about 5 ng/ml to about 260 ng/ml. Although the inventors have not obtained sufficient data for concentrations less than 5 ng/ml to show the effectiveness of the active ingredient in rat ischemic stroke models, the invention may be useful even below this concentration.

When the free plasma concentration of unchanged form is more than about 260 ng/ml, then there is a possibility that the active ingredient may be toxic in monkeys. However, even above this concentration, the invention may be effective and useful in other embodiments—for example (and not limiting the scope of the invention), in pharmaceutical compositions comprising combination of a compound according to the invention and another component.

Other embodiments of the invention for the treatment of ischemic stroke and related causes of insufficient cerebral circulation generally may be administered as described above.

Still other embodiments of a pharmaceutical composition according to the invention for the treatment of disorders associated with syndromes such as ischemic stroke are mentioned below. The active ingredient may be administered at a starting dose of from about 0.025 to about 1.3 mg per kg of the weight of a patient, preferably from about 0.05 to about 0.8 mg per kg of the weight of a patient, more preferably from about 0.075 to about 0.5 mg per kg of the weight of a patient, even more preferably from about 0.1 to about 0.3 mg per kg of the weight of a patient. It is preferred that the mode of administration in such case is intravenous bolus administration. After initiation of administration of the intravenous bolus, it is desirable that the active ingredient is administered at a dose of from about 0.05 to about 2.5 mg/hr per kg of the weight of the patient, preferably from about 0.125 to about 2.0 mg/hr per kg of the weight of the patient, more preferably from about 0.15 to about 1.0 mg/hr per kg of the weight of the patient, even more preferably from about 0.25 to about 0.75 mg/hr per kg of the weight of the patient.

Also preferably, the administration mode in this stage is intravenous infusion. It is desirable that the continuation of administration by intravenous infusion extends for about 0.5 hour, preferably about 1 hour, more preferably about 2.75 hours, even more preferably about 3 hours, still more preferably about 12 hours, further more preferably about 24 hours, still further more preferably about 72 hours, still further more preferably about 120 hours.

The pyrazolone compound of formula (I) of the invention serving as an active ingredient in the invention can be produced in any desired method. Preferred examples of the production method are described in JP-B 5-35128.

A free-form pyrazolone derivative of formula (I) may be used for the active ingredient in the invention. Alternatively, any desired pseudo-polymorphic form, such as a hydrate or solvate, or any combination thereof, or a physiologically acceptable salt of a pyrazolone compound of formula (I) or pseudo-polymorphic form, or their respective combination, may also be used.

The pyrazolone compound includes tautomeric isomers shown by the chemical structural formulae in JP-B 5-31523, column 5, upper section—formula (I') or (I") shown immediately below:

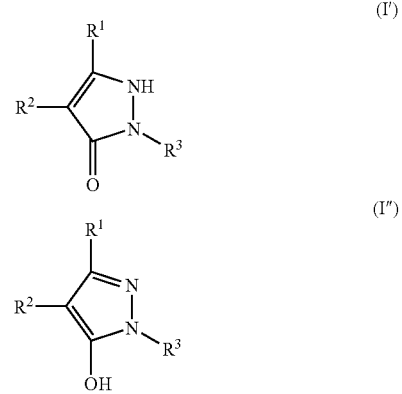

The active ingredient according to the present invention encompasses all these isomers. In formula (I), the aryl group for $R^1$ includes a phenyl group and a phenyl group substituted with a substituent that includes a methyl group, a butyl group, a methoxy group, a butoxy group, a chlorine atom and a hydroxyl group.

The alkyl group having from 1 to 5 carbon atoms for $R^1$, $R^2$ and $R^3$ includes a methyl group, an ethyl group, a propyl group, an isopropyl group, a butyl group, an isobutyl group, a sec-butyl group, a tert-butyl group, a pentyl group.

The alkoxycarbonylalkyl group having from 3 to 6 carbon atoms in total for $R^1$ includes a methoxycarbonylmethyl group, an ethoxycarbonylmethyl group, a propoxycarbonylmethyl group, a methoxycarbonylethyl group, a methoxycarbonylpropyl group.

The aryloxy group for $R^2$ includes a phenoxy group, a p-methylphenoxy group, a p-methoxyphenoxy group, a p-chlorophenoxy group, a p-hydroxyphenoxy group; the arylmercapto group includes a phenylmercapto group, a p-methylphenylmercapto group, a p-methoxyphenylmercapto group, a p-chlorophenylmercapto group, a p-hydroxyphenylmercapto group.

The alkylene group having from 3 to 5 carbon atoms for $R^1$ and $R^2$ includes a trimethylene group, a tetramethylene group, a pentamethylene group, a methyltrimethylene group, an ethyltrimethylene group, a dimethyltrimethylene group, a methyltetramethylene group.

The hydroxyalkyl group having from 1 to 3 carbon atoms for $R^2$ and $R^3$ includes a hydroxymethyl group, a 2-hydroxyethyl group, a 3-hydroxypropyl group. The cycloalkyl group having from 5 to 7 carbon atoms for $R^3$ includes a cyclopentyl group, a cyclohexyl group, a cycloheptyl group.

The alkoxy group having from 1 to 5 carbon atoms for the substituent of the phenyl group for $R^3$ includes a methoxy group, an ethoxy group, a propoxy group, an isopropoxy group, a butoxy group, a pentyloxy group; the alkoxycarbonyl group having from 2 to 5 carbon atoms in total includes a methoxycarbonyl group, an ethoxycarbonyl group, a propoxycarbonyl group, a butoxycarbonyl group; the alkylmercapto group having from 1 to 3 carbon atoms includes a methylmercapto group, an ethylmercapto group, a propylmercapto group; the alkylamino group having from 1 to 4 carbon atoms includes a methylamino group, an ethylamino group, a propylamino group, a butylamino group; the dialkylamino group having from 2 to 8 carbon atoms in total includes a dimethylamino group, a diethylamino group, a dipropylamino group, a dibutylamino group.

Specific examples of the compound of formula (I) for use in the invention are mentioned, but not limited to, below:

3-methyl-1-phenyl-2-pyrazolin-5-one,
3-methyl-1-(2-methylphenyl)-2-pyrazolin-5-one,
3-methyl-1-(3-methylphenyl)-2-pyrazolin-5-one,
3-methyl-1-(4-methylphenyl)-2-pyrazolin-5-one,
3-methyl-1-(3,4-dimethylphenyl)-2-pyrazolin-5-one,
1-(4-ethylphenyl)-3-methyl-2-pyrazolin-5-one,
3-methyl-1-(4-propylphenyl)-2-pyrazolin-5-one,
1-(4-butylphenyl)-3-methyl-2-pyrazolin-5-one,
1-(3-trifluoromethylphenyl)-3-methyl-2-pyrazolin-5-one,
1-(4-trifluoromethylphenyl)-3-methyl-2-pyrazolin-5-one,
1-(2-methoxyphenyl)-3-methyl-2-pyrazolin-5-one,
1-(3-methoxyphenyl)-3-methyl-2-pyrazolin-5-one,
1-(4-methoxyphenyl)-3-methyl-2-pyrazolin-5-one,
1-(3,4-dimethoxyphenyl)-3-methyl-2-pyrazolin-5-one,
1-(4-ethoxyphenyl)-3-methyl-2-pyrazolin-5-one,
3-methyl-1-(4-propoxyphenyl)-2-pyrazolin-5-one,
1-(4-butoxyphenyl)-3-methyl-2-pyrazolin-5-one,
1-(2-chlorophenyl)-3-methyl-2-pyrazolin-5-one,
1-(3-chlorophenyl)-3-methyl-2-pyrazolin-5-one,
1-(4-chlorophenyl)-3-methyl-2-pyrazolin-5-one,
1-(3,4-dichlorophenyl)-3-methyl-2-pyrazolin-5-one,
1-(4-bromophenyl)-3-methyl-2-pyrazolin-5-one,
1-(4-fluorophenyl)-3-methyl-2-pyrazolin-5-one,
1-(3-chloro-4-methylphenyl)-3-methyl-2-pyrazolin-5-one,
1-(3-methylmercaptophenyl)-3-methyl-2-pyrazolin-5-one,
1-(4-methylmercaptophenyl)-3-methyl-2-pyrazolin-5-one,
4-(3-methyl-5-oxo-2-pyrazolin-1-yl)benzoic acid,
1-(4-ethoxycarbonylphenyl)-3-methyl-2-pyrazolin-5-one,
1-(4-nitrophenyl)-3-methyl-2-pyrazolin-5-one
3-ethyl-1-phenyl-2-pyrazolin-5-one,
1-phenyl-3-propyl-2-pyrazolin-5-one;
1,3-diphenyl-2-pyrazolin-5-one,
3-phenyl-1-(p-tolyl)-2-pyrazolin-5-one,
1-(4-methoxyphenyl)-3-phenyl-2-pyrazolin-5-one,
1-(4-chlorophenyl)-3-phenyl-2-pyrazolin-5-one,
3,4-dimethyl-1-phenyl-2-pyrazolin-5-one,
4-isobutyl-3-methyl-1-phenyl-2-pyrazolin-5-one,
4-(2-hydroxyethyl)-3-methyl-1-phenyl-2-pyrazolin-5-one,
3-methyl-4-phenoxy-1-phenyl-2-pyrazolin-5-one,
3-methyl-4-phenylmercapto-1-phenyl-2-pyrazolin-5-one,
2,3a,4,5,6,7-hexahydro-2-phenylindazol-3-one,
3-(ethoxycarbonylmethyl)-1-phenyl-2-pyrazolin-5-one,
1-phenyl-2-pyrazolin-5-one,
3-methyl-2-pyrazolin-5-one,
1,3-dimethyl-2-pyrazolin-5-one,
1-ethyl-3-methyl-2-pyrazolin-5-one,
1-butyl-3-methyl-2-pyrazolin-5-one,
1-(2-hydroxyethyl)-3-methyl-2-pyrazolin-5-one,
1-cyclohexyl-3-methyl-2-pyrazolin-5-one,
1-benzyl-3-methyl-2-pyrazolin-5-one,
1-(α-naphthyl)-3-methyl-2-pyrazolin-5-one,
1-methyl-3-phenyl-2-pyrazolin-5-one,
3-methyl-1-(4-methylphenyl)-2-pyrazolin-5-one,
1-(4-butylphenyl)-3-methyl-2-pyrazolin-5-one,
1-(4-methoxyphenyl)-3-methyl-2-pyrazolin-5-one,
1-(4-butoxyphenyl)-3-methyl-2-pyrazolin-5-one,
1-(4-chlorophenyl)-3-methyl-2-pyrazolin-5-one,
1-(4-hydroxyphenyl)-3-methyl-2-pyrazolin-5-one,
1-(3,4-dihydroxyphenyl)-3-methyl-2-pyrazolin-5-one,
1-(2-hydroxyphenyl)-3-methyl-2-pyrazolin-5-one,
1-(3-hydroxyphenyl)-3-methyl-2-pyrazolin-5-one,
1-(4-hydroxyphenyl)-3-methyl-2-pyrazolin-5-one,
1-(3,4-hydroxyphenyl)-3-methyl-2-pyrazolin-5-one,
1-(4-hydroxyphenyl)-3-phenyl-2-pyrazolin-5-one,
1-(4-hydroxymethylphenyl)-3-methyl-2-pyrazolin-5-one,
1-(4-aminophenyl)-3-methyl-2-pyrazolin-5-one,
1-(4-methylaminophenyl)-3-methyl-2-pyrazolin-5-one,
1-(4-ethylaminophenyl)-3-methyl-2-pyrazolin-5-one,
1-(4-butylaminophenyl)-3-methyl-2-pyrazolin-5-one,
1-(4-dimethylaminophenyl)-3-methyl-2-pyrazolin-5-one,
1-(acetamidophenyl)-3-methyl-2-pyrazolin-5-one,
1-(4-cyanophenyl)-3-methyl-2-pyrazolin-5-one.

Pharmaceutically acceptable salts of the pyrazolone compound of formula (I) may be acid-addition salts or base-addition salts. For example, they include mineral acid salts such as hydrochlorides, sulfates, hydrobromides or phosphates; organic acid salts such as methanesulfonates, para-toluenesulfonates, acetates, oxalates, citrates, maleates or fumarates; metal salts such as sodium salts, potassium salts or magnesium salts; ammonium salts; and organic amine salts with ethanolamine or 2-amino-2-methyl-1-propanol. With no specific limitation thereon, all salts that are pharmaceutically acceptable for use of the pyrazolone compound of formula (I) of the invention are usable within the scope of the invention.

As the active ingredient of the drug of the invention, one or more different types of a compound of formula (I) or a pharmaceutically acceptable salt thereof or a pseudo-polymorphic or other physical form or forms mentioned above may be directly administered to patients, but preferably, the active ingredient is combined with a pharmacologically and pharmaceutically acceptable additive and formulated into a pharmaceutical preparation well known to those skilled in the art.

The pharmacologically and pharmaceutically acceptable additive includes, for example, vehicle, disintegrator or disintegration aid, binder, lubricant, coating agent, dye, diluent, base, solubilizer or dissolution aid, isotonizer, pH-controlling agent, stabilizer, propellant and adhesive. Examples of the preparation suitable to oral administration are tablets, capsules, powder, fine granules, granules, liquids, and syrups. Examples of the preparation suitable to parenteral administration are injections, drips, plasters, and suppositories. Preferred examples are plasters and injections. More preferred examples are injections.

The additive to the preparation suitable to oral administration includes, for example, vehicle such as glucose, lactose, D-mannitol, starch or crystalline cellulose; disintegrator or disintegration aid such as carboxymethyl cellulose, starch or calcium carboxymethyl cellulose; binder such as hydroxypropyl cellulose, hydroxypropylmethyl cellulose, polyvinylpyrrolidone or gelatin; lubricant such as magnesium stearate or talc; coating agent such as hydroxypropylmethyl cellulose, white sugar, polyethylene glycol or titanium oxide; base such as vaseline, liquid paraffin, polyethylene glycol, gelatin, kaolin, glycerin, pure water or hard fat.

In the preparation suitable for injections or drips, usable are various preparation additives, for example, solubilizer or dissolution aid to constitute aqueous injections or in-situ dissolution injections, such as distilled water for injections, physiological saline or propylene glycol; isotonizer such as glucose, sodium chloride, D-mannitol, glycerin; and pH-controlling agent such as inorganic acids, organic acids, inorganic bases or organic bases.

BEST MODE FOR CARRYING OUT THE INVENTION

Embodiments of the invention are set out below in the following Examples and test Examples, without limitation of the scope of the invention.

Synthesis Example 1

Synthesis of 1-phenyl-3-methyl-2-pyrazolin-5-one (Edaravone)

To 50 ml of ethanol were added 13.0 g of ethyl acetacetate and 10.8 g of phenylhydrazine, followed by stirring under reflux for 3 hours. After the reaction mixture was allowed to cool down, crystals thus precipitated were collected by filtration and recrystallized from ethanol, whereby 11.3 g of the title compound was obtained as colorless crystals.

Yield: 67%.

Melting point: 127.5 to 128.5° C.

Example 1

Administration: Effectiveness Against Cerebral Edema in a Rat Middle Cerebral Artery Occlusion and Reperfusion Model After eight weeks to nine weeks old Wistar rats (220 to 260 g) were subjected to inhalation anesthesia with halothane, the inhalation anesthesia with 1% halothane (anesthesia; nitrous oxide: oxygen=7:3) was continued while fixing them in a dorsal position and maintaining their body temperature at around 37° C. In an infusion administration group and a bolus+infusion administration group, a catheter was placed in the femora vein. The right common carotid artery, external carotid artery and internal carotid artery were exposed and the common carotid artery and external carotid artery were ligated in order to occlude the middle cerebral artery. From the common carotid artery, a No. 4 nylon suture (plug) was inserted to occlude the middle cerebral artery. Three hours after occlusion of the middle cerebral artery, the plug was taken out from the common carotid artery and perfusion of the middle cerebral artery was resumed, and then the administration was started as in Table 3. Decapitation and surgical removal of the brain were performed three hours after reperfusion. After separation of the right and left cerebral cortex, the wet weight was measured. After drying at 130° C. for 24 hours, the dry weight was determined. A percentage water content was calculated in accordance with the following equation: (wet weight (g)−dry weight (g))/wet weight (g)× 100. The constitution and dose of each group are shown below in Table 3. It is to be noted that to the drug administered groups other than the control group, Edaravone was administered as a drug in accordance with Table 3.

TABLE 3

| Group | Dose | Starting time of administration and administration time |
|---|---|---|
| Control | — | — |
| Bolus | 3 mg/kg, i.v. | Bolus immediately after reperfusion started |
| Infusion | 1 mg/kg/hr, i.v. | Infusion for 3 hours immediately after reperfusion started |
| Bolus + infusion | 0.2 mg/kg, i.v. + 1 mg/kg/hr, i.v. | Bolus of 0.2 mg/kg immediately after reperfusion started, followed by infusion for 2.75 hours |

The results are shown in FIG. 1. As is apparent from FIG. 1, in each group, the percentage water content of rat's cortex to which an ischemic load had been applied showed an increase. An increase in the percentage water content was greatest in the control group. It was almost equal in the bolus group and the infusion group, and was lowest in the bolus+ infusion group. The total dose of the drug in the drug administered groups other than the control group was 3 mg/kg in the bolus group and also 3 mg/kg (1 mg/kg/hr×3 hr) in the infusion group, while in the bolus+infusion group, it was 2.95 mg/kg (0.2 mg/kg+1 mg/kg/hr×2.75 hr). This has revealed that the percentage water content of the bolus+infusion group was lowest though the dose of the drug was smallest of all the groups.

Example 2

Measurement of the Plasma Concentration of Unchanged Form of the Compound in Rat Eight weeks to nine weeks old Wistar rats (230 to 250 g) were classified into three groups, that is, a bolus group, an infusion group and a bolus+infusion group. In accordance with Table 3 of Example 1, 30 mg (30 mg of Edaravone/20 ml) of commercially available Radicut® (trade name) injection 30 mg was intravenously administered. Under anesthesia with ether, the blood was collected 3 minutes, 30 minutes, 1 hour and 2.75 hours after initiation of administration for each group. The plasma concentration of unchanged form of the compound in the sample thus collected was measured by the LC-MS/MS method. The measurement conditions are shown in Table 4, while the measurement results are shown in FIG. 2-*a* and FIG. 2-*b*.

TABLE 4

| | |
|---|---|
| Column | CAPCELL PAC C18MG 2.0 mm (ID) × 150 mm (Shiseido Co.) |
| Mobile Phase | methanol/10 mmol/L ammonium acetate (pH 4.5) (4:6, v/v) |
| Flow Rate | 0.2 mL/min |
| Column Temperature | 50° C. |
| Auto sampler Temperature | 4° C. |
| Spray Voltage | 5.0 kV |
| Sheath Gas Pressure | 37 Torr |
| Auxiliary Gas Pressure | 16 Torr |
| Capillary Temperature | 397° C. |
| Scan Mode | SRM |
| Ionization Method | ESI (positive) |

Based on the facts that the active form of Edaravone is the unchanged form, (Japanese Pharmacology & Therapeutics, Vol. 25, Supplement 1997, pp. 209-211) and in general, the active form does not exhibit drug efficacy when the active form combined with protein existing in the blood, the free plasma concentration of unchanged form of the compound was calculated based on the measurement results of the plasma concentration of unchanged form of the compound in the rat; and from the value thus obtained, the human plasma concentration of unchanged form of the compound was calculated. The results are shown in FIG. 3-*a* and FIG. 3-*b*. The binding ratios of rat and human serum proteins with Edaravone are set at 85.8% and 91.9%, respectively, in accordance with Japanese Pharmacology & Therapeutics, Vol. 25, Supplement 1997, pp. 245-254. The human plasma concentration of unchanged form of the compound was found from the following equation: the human plasma concentration of unchanged form of the compound=rat plasma concentration of unchanged form of the compound×(1-0.858)/(1-0.919).

Example 3-1

Dose Response Test with Rat

Seven weeks to eight weeks old Crj:CD(SD) male rats (190 to 250 g) were subjected to anesthesia with isoflurane, and were fixed in a dorsal position with their body temperature kept at around 37° C. A catheter for drug administration was placed in the cervical vein. The right common carotid artery, external carotid artery and internal carotid artery were exposed and the common carotid artery and external carotid artery were ligated in order to occlude the middle cerebral artery. From the branch of the external carotid artery and the internal carotid artery, a silicone-coated No. 4 nylon suture (plug) was inserted to occlude the middle cerebral artery. Two hours after occlusion of the middle cerebral artery, the plug was taken out and perfusion of the middle cerebral artery was resumed, and then the administration was started as in Table 5. Decapitation and surgical removal of the brain were performed 24 hours after reperfusion. Five brain sections each having a thickness of 2 mm (from the bregma part, from 2 mm before and behind parts of the bregma, and from 4 mm before and behind parts of the bregma) were prepared. The brain sections were stained with 1 w/v % 2,3,5-triphenyltetrazolium chloride, and the infarct area was measured to calculate the infarct volume.

The group constitution and the dose are shown in Table 5 below. In the drug administered groups than the control group with physiological saline alone administration, Edaravone was used as the drug and this was administered as in Table 5.

TABLE 5

| Drug | loading dose (i.v.) | | maintenance dose (i.v.) | |
|---|---|---|---|---|
| | dose weight | dose volume | dose weight | dose volume |
| physiological saline | | 1.0 ml/kg | | 0.5 ml/body/hr |
| Edaravone | 0.05 mg/kg | 1.0 ml/kg | 0.25 mg/kg/hr | 0.5 ml/body/hr |
| Edaravone | 0.1 mg/kg | 1.0 ml/kg | 0.5 mg/kg/hr | 0.5 ml/body/hr |
| Edaravone | 0.2 mg/kg | 1.0 ml/kg | 1.0 mg/kg/hr | 0.5 ml/body/hr |

The results are shown in FIG. 4. As compared with that in the control group with physiological saline alone administration, the infarct volume in the Edaravone administered groups was small, and the infarct area significantly decreased in the Edaravone 0.1 mg/kg+0.5 mg/kg/hr administered group (P<0.05).

Example 3-2

Dose Response Test with Monkey

A croo monkey (3 years to 5 years old) was subjected to inhalation anesthesia with pentobarbital, and then its body temperature was kept at around 37° C. The middle cerebral artery at around the branch of the left internal carotid artery was exposed, and the middle cerebral artery was occluded by electrocoagulation. Then, the administration was started as in Table 6. 28 hours after occlusion (just after administration), the whole brain was removed under deep anesthesia by excess pentobarbital administration, and coronary brain sections each having a thickness of 4 mm were cut out of the forehead. The brain sections were stained with 1 w/v % 2,3,5-triphenyltetrazolium chloride, and the infarct area was measured to calculate the infarct volume.

The group constitution and the dose are shown in Table 6 below. In the drug administered groups other than the solvent group, Edaravone was used as the drug and this was administered as in Table 6.

TABLE 6

| Drug | loading dose (i.v.) | | maintenance dose (i.v.) | |
|---|---|---|---|---|
| | dose weight | dose volume | dose weight | dose volume |
| solvent | | 1.0 ml/kg | | 2.0 ml/kg/hr |
| Edaravone | 0.1 mg/kg | 1.0 ml/kg | 0.5 mg/kg/hr | 2.0 ml/kg/hr |
| Edaravone | 0.2 mg/kg | 1.0 ml/kg | 1.0 mg/kg/hr | 2.0 ml/kg/hr |
| Edaravone | 0.4 mg/kg | 1.0 ml/kg | 2.0 mg/kg/hr | 2.0 ml/kg/hr |

The results are shown in FIG. 5. As compared with that in the control group with solvent alone administration, the infarct volume in the Edaravone administered groups was small.

Example 4

Dose Simulation

From the results of the bolus+infusion group in Example 2, the plasma concentration of unchanged form of the compound at this dose used Radicut® is from 163.7 to 174.7 ng/ml. In consideration of the rat protein binding percentage (85.8%), the free plasma concentration of unchanged form of the compound is calculated to be from 23.3 to 24.8 ng/ml. The human plasma concentration of unchanged form of the compound (protein binding percentage, 91.9%) that may be on the same level as that of the free plasma concentration of unchanged form of the compound is from 287.7 to 306.2 ng/ml, and the monkey plasma concentration of unchanged form of the compound (protein binding percentage, 87.4%) is from 184.9 to 196.8 ng/ml. The loading dose (the time necessary for administration at the loading dose is considered to be 0 minute) and the maintenance dose that give these human and monkey plasma concentrations of unchanged form of the compound are presumed from the pharmacokinetic parameters (distribution volume, rate constant). The pharmacokinetic parameter calculation and the simulation of the plasma concentration of unchanged form of the compound in maintenance dose administration after loading dose administration were carried out by the use of the pharmacokinetic analysis software WinNonlin ver. 4.0 (supplied by Pharsight Corporation).

For the monkey data, the pharmacokinetic parameter was obtained from the plasma concentration of unchanged form of the compound in 2 mg/kg bolus administration and 2 mg/kg/2 hr infusion administration of Edaravone to healthy monkey. Using the pharmacokinetic parameter in 2 mg/kg bolus administration, the plasma concentration of unchanged form of the compound at a loading dose of 0.1 mg/kg was simulated (A). Next, using the pharmacokinetic parameter in 2 mg/kg/2 hr infusion administration, the plasma concentration of unchanged form of the compound at a maintenance dose of 0.5 mg/kg/hr was simulated (B). (A) and (B) are summed, and the plasma concentration of unchanged form of the compound is presumed to be approximately 220 ng/ml.

For humans, the pharmacokinetic parameter was obtained from the plasma concentration of unchanged form of the compound in 1.5 mg/kg/40 min and 1.8 mg/kg/6 hr infusion administration of Edaravone to healthy adults. Using the pharmacokinetic parameter in 1.5 mg/kg/40 min infusion administration, the plasma concentration of unchanged form of the compound at a loading dose of 0.1 mg/kg was simulated (C). Next, using the pharmacokinetic parameter in 1.8 mg/kg/6 hr infusion administration, the plasma concentration of unchanged form of the compound at a maintenance dose of 0.25 mg/kg was simulated (D). (C) and (D) are summed, and the plasma concentration of unchanged form of the compound is presumed to be approximately 318 ng/ml.

Test Example 1

Clinical Test with Human

Edaravone is first administered to healthy humans, and Edaravone and its main metabolites are analyzed for their endokinetics and safety. In this stage, the dose is appropriately controlled so as to obtain the intended plasma concentration of unchanged form. With reference to the data obtained in this stage, the dose to be employed in the next stage is investigated (first step). Next, Edaravone is investigated for its safety to ischemic stroke patients at their acute stage (second step). In the first step and the second step, the dose and the administration period are stepwise increased. With reference to the information data obtained in the tests of the first step and the second step, some doses are selected, and these are subjected to comparison test for their efficacy and the safety. Based on this, the dose to be investigated in the next step is specifically defined (third step). Finally, the dose specifically defined in the previous step is investigated for its efficacy (fourth step).

INDUSTRIAL APPLICABILITY

This invention is useful as a method for treatment of cerebrovascular disorders associated with insufficient cerebral circulation.

While the invention has been described in detail and with reference to specific embodiments thereof, it will be apparent to one skilled in the art that various changes and modifications can be made therein without departing from the spirit and scope thereof.

This application is based on Japanese patent application No. 2004-233635 filed on Aug. 10, 2004, the entire contents thereof being hereby incorporated by reference.

BRIEF DESCRIPTION OF THE DRAWINGS

FIG. 2-*a* illustrates the measurement results (Example 2) of the rat plasma concentration of unchanged form.

FIG. 2-*b* illustrates the rat plasma concentration of unchanged form obtained from the infusion group and Bolus+infusion group of FIG. 2-*a*.

(Note that the scale of the vertical bar is different from that in FIG. 2-*a*)

FIG. 3-*a* illustrates the human plasma concentration of unchanged form calculated from the measurement results of the rat plasma concentration of unchanged form.

FIG. 3-*b* illustrates the human plasma concentration of unchanged form obtained from the infusion group and Bolus+infusion group of FIG. 3-*a*.

(Note that the scale of the vertical bar is different from that in FIG. 3-*a*)

Figure 1:
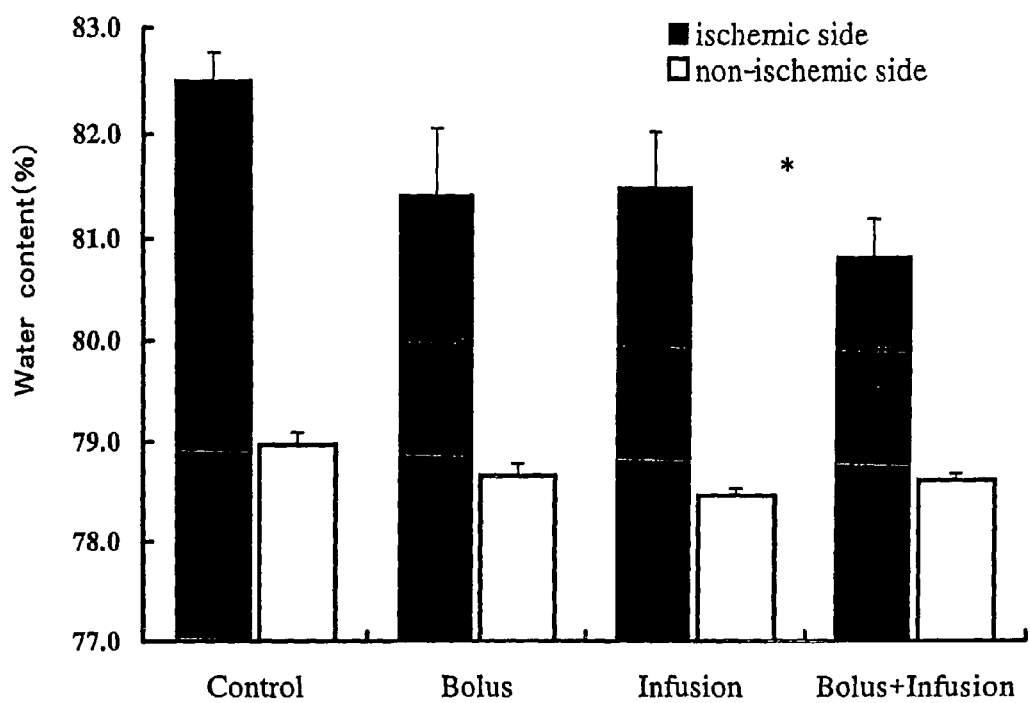
FIG. 1 illustrates the results of the consideration (Example 1) on the action against cerebral edema in a rat middle cerebral artery occlusion and reperfusion model.
Figure 4:
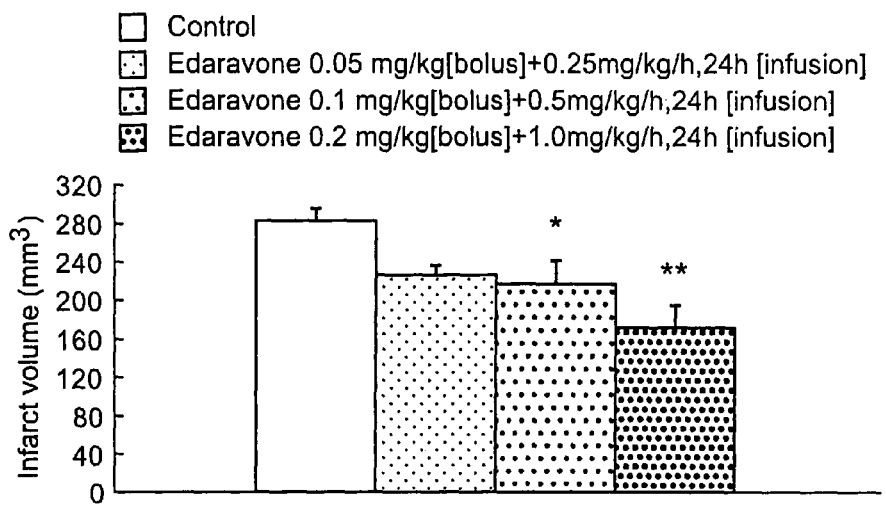

FIG. 4 illustrates the results of the rat dose response test in Example 3-1.

Figure 5:
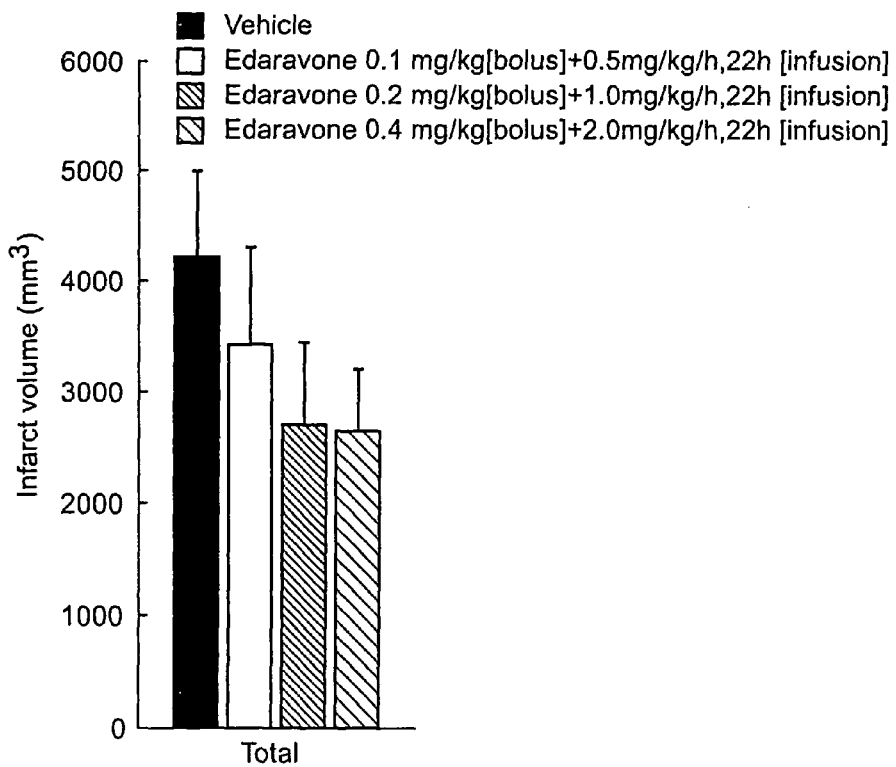

FIG. 5 illustrates the results of the monkey dose response test in Example 3-2.

The invention claimed is:

1. A method for the treatment of a brain with acute ischemic stroke, or a method for the treatment of a brain after acute ischemic stroke to reduce cerebral infarcts, comprising administration to a patient in need of such treatment of a therapeutically effective amount of 3-methyl-1-phenyl-2-pyrazolin-5-one, which comprises an administration of a loading dose by intravenous bolus administration which is finished within about five minutes and an administration of a maintenance dose by intravenous continuous administration for about 24 hours to 120 hours, wherein the dose administered by the loading dose administration is about 0.05 to about 0.5 mg per kg of the weight of a patient, and the dose administered by the administration of the maintenance dose is about 0.125 to about 2.0 mg/hr per kg of the weight of the patient.

2. The method according to claim 1, wherein the duration of the administration of the maintenance dose is about 24 hours to about 72 hours.

3. The method according to claim 1, wherein the dose administered by the loading dose administration is selected from the group consisting of about 0.075 to about 0.4 mg per kg of the weight of a patient and about 0.1 to about 0.3 mg per kg of the weight of a patient.

4. The method according to claim 1, wherein the dose administered by the administration of the maintenance dose is selected from the group consisting of about 0.15 to about 1.0 mg/hr per kg of the weight of the patient and about 0.25 to about 0.75 mg/hr per kg of the weight of the patient.

5. A method for the treatment of a brain with acute ischemic stroke, or a method for the treatment of a brain after acute ischemic stroke to reduce cerebral infarcts, comprising administration, to a patient in need of such treatment, of a loading dose and a maintenance dose of a therapeutically effective amount of 3-methyl-1-phenyl-2-pyrazolin-5-one, wherein the administration of the loading dose is intravenous bolus administration which is finished within about five minutes, and further wherein the dose administered by the loading dose administration is selected from the group consisting of about 0.05 to about 0.5 mg per kg of the weight of a patient and about 0.075 to about 0.4 mg per kg of the weight of a patient; the dose administered by the administration of the maintenance dose is selected from the group consisting of about 0.125 to about 2.0 mg/hr per kg of the weight of the patient, about 0.15 to about 1.0 mg/hr per kg of the weight of the patient, and about 0.25 to about 0.75 mg/hr per kg of the weight of the patient; and the maintenance dose is administered by intravenous infusion administration for a duration which is selected from the group consisting of about 120 hours, about 72 hours, and about 24 hours, after initiation of administration of the maintenance dose.

6. The method according to claim 5, wherein patients in need of such treatment are determined by NIH stroke scale of not more than 22, or by a method of determination for neurological criticality corresponding to the NIH stroke scale of not more than 22.

7. The method according to claim 1, wherein a duration of the administration of the maintenance dose is 72 hours to 120 hours.

* * * * *